US012746199B2

(12) United States Patent
Kondaveeti et al.

(10) Patent No.: US 12,746,199 B2
(45) Date of Patent: Sep. 29, 2026

(54) LIQUID, STORAGE STABLE, DIRECTLY INJECTABLE, PANTOPRAZOLE FORMULATIONS, THEIR USES AND MANUFACTURING

(71) Applicants: Etico Lifesciences Private Limited, Hyderbaad (IN); Hyloris Developments SA, Liege (BE)

(72) Inventors: Soumya Kondaveeti, Hyderbaad (IN); Sravan Kumar Thondapu, Hyderbaad (IN); Ajay Kumar Bachupally, Hyderbaad (IN); Shanmukha Srinivas Mule, Hyderbaad (IN); Venkata Radha Krishna Bodagala, Hyderbaad (IN); Atul Patil, Liege (BE)

(73) Assignees: Etico Lifesciences Private Limited, Hyderbaad (IN); Hyloris Developments SA, Liege (BE)

( * ) Notice: Subject to any disclaimer, the term of this patent is extended or adjusted under 35 U.S.C. 154(b) by 0 days.

(21) Appl. No.: 19/394,021

(22) Filed: Nov. 19, 2025

(65) Prior Publication Data

US 2026/0076902 A1 Mar. 19, 2026

Related U.S. Application Data

(63) Continuation of application No. PCT/EP2025/055608, filed on Feb. 28, 2025, and a continuation of application No. PCT/EP2024/056382, filed on Mar. 11, 2024.

(51) Int. Cl.

| | |
|---|---|
| ***A61K 9/08*** | (2006.01) |
| ***A61K 9/00*** | (2006.01) |
| ***A61K 31/4439*** | (2006.01) |
| ***A61K 47/02*** | (2006.01) |
| ***A61K 47/10*** | (2017.01) |

(52) U.S. Cl.

CPC .............. *A61K 9/08* (2013.01); *A61K 9/0019* (2013.01); *A61K 31/4439* (2013.01); *A61K 47/02* (2013.01); *A61K 47/10* (2013.01)

(58) Field of Classification Search

None

See application file for complete search history.

(56) References Cited

U.S. PATENT DOCUMENTS

| | | | | |
|---|---|---|---|---|
| 6,730,685 | B1 | 5/2004 | Brulls | |
| 6,780,881 | B2 | 8/2004 | Linder et al. | |
| 2004/0186139 | A1 * | 9/2004 | Reddy ................ | A61K 31/4439 546/273.7 |

OTHER PUBLICATIONS

PCT/EP2025/055608, International Search Report, mailed May 22, 2025.

* cited by examiner

*Primary Examiner* — Isis A Ghali

(74) *Attorney, Agent, or Firm* — Vance Intellectual Property, PC

(57) ABSTRACT

The present invention provides a concentrated, storage stable, liquid composition of pantoprazole or a pharmaceutically acceptable salt thereof. The invention further provides uses for the composition, and packaging containers comprising the composition. In particular, the present invention relates to stable pantoprazole sodium formulations with controlled room temperature as storage condition, in the form of a ready-to-use liquid solution or in the form of a ready-to-dilute formulation, for dilution with infusion solution, processes for their preparation and use.

11 Claims, No Drawings

LIQUID, STORAGE STABLE, DIRECTLY INJECTABLE, PANTOPRAZOLE FORMULATIONS, THEIR USES AND MANUFACTURING

FIELD OF THE INVENTION

The present invention relates to concentrated liquid compositions comprising the proton pump inhibitor pantoprazole. The compositions have prolonged storage stability and are directly injectable. Upon dilution with a suitable diluent, solutions are obtained with physiologically compatible pH and osmolality. Accessibility to care givers and patients is drastically improved. Patient comfort is increased. The invention is beneficial to the field of pharmaceutical preparations and uses thereof.

Stable concentrated liquid injectable formulations with controlled room temperature as storage conditions are provided. The compositions are stable ready-to-use liquid solutions, and/or ready for dilution with infusion solution. In addition, the invention provides processes for their preparation and use, as well as packaging containers comprising the composition.

BACKGROUND OF THE INVENTION

Benzimidazole-based proton pump inhibitors (PPIs) share a common structural element, the benzimidazole ring. Some examples of benzimidazole PPI compounds are Pantoprazole, Omeprazole, Lansoprazole, Rabeprazole and Esomeprazole. Pantoprazole sodium sesquihydrate is a substituted benzimidazole, sodium 5-(difluoromethoxy)-2-[[(3,4-dimethoxy-2-pyridinyl)methyl] sulfinyl]-1H-benzimidazole, a compound that inhibits gastric acid secretion having the chemical structure:

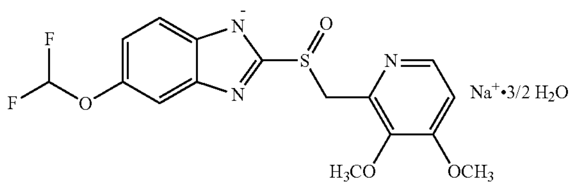 [SMILES: COc1ccnc(CS(=O)c2nc3cc(OC(F)F)ccc3[nH]2)c1OC]

Major challenges associated with PPI injection formulations are hydrolysis and thermal instability, necessitating freeze-dried/lyophilized formulations.

Pantoprazole Sodium injectable dosage form is commercially available as a sterile freeze-dried/lyophilized powder or cake and sold as 40 mg/vial (equivalent to 45.1 mg of pantoprazole sodium). Pantoprazole sodium powder for injection is labeled for administration as an infusion (4 mg/mL for gastroesophageal reflux disease (GERD) or pathological hypersecretion, respectively) or as a 15-minute infusion (0.4 mg/mL or 0.8 mg/mL or 1.3 mg/mL for GERD or pathological hypersecretion, respectively). The 2 min administration requires a reconstitution step with 0.9% Sodium Chloride Injection and the 15-minute infusion requires a second dilution in one of the following: 5% Dextrose Solution for Injection or 0.9% Sodium Chloride Solution for Injection.

U.S. Pat. No. 6,780,881 discloses the lyophilized pantoprazole preparations which are obtainable by freeze-drying of an aqueous solution of pantoprazole, ethylenediamine tetra acetic acid and/or a suitable salt thereof, and sodium hydroxide and/or sodium carbonate.

The existing technology for preparing pantoprazole sodium for injection (e.g., 40 mg/vial) is freeze drying which requires reconstitution prior to intravenous injection or infusion. Further, the lyophilization process employed for the preparation of the freeze-dried/lyophilized powder or cake is costly and complex. The process of reconstitution of existing lyophilized formulation of pantoprazole sodium requires several lengthy and complicated preparation steps that comprises reconstitution of each vial and subsequent dilution into an infusion bag. Additionally, the reconstituted formulation has limited stability.

Further, the lyophilization/freeze drying process requires complex and time-consuming steps to obtain sterile freeze-dried product which increases the commercial cost of the product.

In the United States, it exists a commercially available frozen, ready-to-use single-dose bag of pantoprazole sodium in 50 or 100 mL of 0.9% Sodium Chloride designed for intravenous infusion. However, this product has limitations. It is exclusively for intravenous infusion Additionally, the product must be stored, transported, and handled below −20° C. (−4° F.), and it is fragile in its frozen state. Prior to use, the bag must be thawed at room temperature (20° C. to 25° C. or 68° F. to 77° F.) or under refrigeration (2° C. to 8° C. or 36° F. to 46° F.), a process that requires advance planning and is time consuming, requiring the patient to wait for an extended period, which is undesirable when timely administration is crucial for patient care. Further, after thawing, the solution is stable only for 21 days under refrigeration.

Therefore, there is a need in the art to simplify the reconstitution process for the lyophilized formulations of pantoprazole in particular pantoprazole sodium, making it suitable for use over an extended period. Also, there is a need in the art to address the cost and/or complexity associated with the lyophilization process.

There is a need in the art for alternatives. The objective of the present invention is the provision of a long-term stable, pantoprazole composition that can be administered directly by injection or via infusion, without the need for reconstitution of a lyo product or thawing, allowing for a fast administration and easy use. Especially, there is a need for a long-term stable, ready-to-use intravenous formulation designed for bolus injection. Such a composition would allow patients to receive treatment at home, without the need for hospitalization, by enabling self-administration, for instance, through prefilled syringes or pens.

SUMMARY OF THE INVENTION

The present invention provides a composition ready-to-use and/or ready-to-dilute, the composition comprising a pharmaceutically acceptable salt of pantoprazole a solvent system comprising one or more organic solvents, and a stabilizing agent.

The present invention provides a storage stable directly injectable formulation (ready-to-use). The formulation is also ready-to-dilute with infusion solution, without any need for preparation of premix solutions comprising an osmolality adjuster or pH adjuster.

In a first aspect, the invention provides a concentrated, storage stable, non-aqueous composition of pantoprazole comprising:

20-80 mg of a pharmaceutically acceptable salt of pantoprazole (API), expressed in amount of pantoprazole, polyethylene glycol in a quantity for the dissolution of the API, optionally a stabilizer, preferably an alkali metal hydroxide, more preferably sodium hydroxide, wherein the composition is comprised in a volume equal to or smaller than 1.0 mL.

The inventors have surprisingly found that a pantoprazole liquid composition comprising polyethylene glycol with a stabilizer, preferably an alkali metal hydroxide, provides a formulation with improved stability, which can be stored at controlled room temperature of 20°-25° C. (68°-77° F.).

Preferably, the volume of the concentrated, storage stable, non-aqueous composition is equal to or smaller than 0.5 mL. Preferably the volume is 0.5 mL.

Preferably, the concentrated, storage stable, non-aqueous composition has a storage stability of at least 1 year measured at 25° C. and 60% relative humidity, wherein the composition contains equal to or less than 4.0% w/w of total impurities, as determined by HPLC.

Preferably, the concentrated, storage stable, non-aqueous composition contains equal or less than 2.5% w/w of impurity C, as determined by HPLC.

Preferably, the pantoprazole salt of the concentrated, storage stable, non-aqueous composition is the pantoprazole sodium salt, more preferably the pantoprazole sodium sesquihydrate salt.

Preferably, the concentrated, storage stable, non-aqueous composition comprises 40 mg of said pharmaceutically acceptable salt of pantoprazole (API) comprised in a volume of 0.5 mL.

Preferably, the amount of stabilizer in the concentrated, storage stable, non-aqueous pantoprazole composition is 0.01 to 1.50 mg/mL, preferably 0.03 to 1.20 mg/mL, even more preferably 0.05 to 0.50 mg/mL, most preferred 0.1 to 0.3 mg/mL.

Preferably, the amount of stabilizer in the concentrated, storage stable, non-aqueous composition is 0.05 to 0.50 mg/mL, preferably 0.1 to 0.3 mg/mL.

More preferably the composition comprises 0.1 to 1.50 mg/mL sodium hydroxide, even more preferably 0.2 to 1.40 mg/mL sodium hydroxide, even more preferably 0.3 to 1.30 mg/mL, also more preferably 0.5 to 1.2 mg/mL; most preferably 0.2 mg/mL.

Preferably, the polyethylene glycol used in the concentrated, storage stable, non-aqueous composition of a pharmaceutically acceptable form of pantoprazole has an average molecular weight below 500, preferably the polyethylene glycol is PEG300 (avg Mw 300).

Preferably, the dissolved oxygen content in the concentrated, storage stable, non-aqueous composition of a pharmaceutically acceptable form of pantoprazole is below 10 ppm, preferably below 5 ppm, most preferably around 2 ppm.

Preferably, the water content in the concentrated, storage stable, non-aqueous composition of a pharmaceutically acceptable form of pantoprazole is equal to or below 4.0% w/v.

In another aspect, the concentrated, storage stable, non-aqueous composition of a pharmaceutically acceptable salt of pantoprazole according to an embodiment of the invention is for use in the treatment of a patient suffering from a gastrointestinal disease, wherein the patient is administered the 1 mL or lower of the composition intravenously without prior dilution.

In another aspect, the invention provides a method of treatment of a patient suffering from a gastrointestinal disease comprising the step of administering a concentrated, storage stable, non-aqueous composition of pharmaceutically acceptable salt of pantoprazole according to an embodiment of the invention, as a bolus injection (ready-to-use).

In another aspect, the invention relates to a method of treatment of a patient suffering from a gastrointestinal disease comprising the step of diluting a concentrated, storage stable, non-aqueous composition of a pharmaceutically acceptable salt of pantoprazole according to an embodiment of the invention with a suitable aqueous diluent to 0.4-4.0 mg/mL pharmaceutically acceptable salt of pantoprazole, expressed as pantoprazole; thereafter administering to the patient the diluted composition obtained, as an infusion (ready-to-dilute).

Preferably, the osmolality of the diluted composition obtained is 200-1000 mOsmol/kg.

Preferably the pH of the diluted composition obtained is 8.2-10.5, most preferably 8.5-10.0.

More preferably a diluted composition, obtained by diluting a concentrated, storage stable, non-aqueous pantoprazole composition according to an embodiment of the invention, has an osmolality of 200-1000 mOsmol/kg and a pH 8.2-10.5.

Most preferably a diluted composition, obtained by diluting a concentrated, storage stable, non-aqueous pantoprazole composition according to an embodiment of the invention, has an osmolality of 220-600 mOsmol/kg and a pH 8.5-10.0.

Preferably in a method according to an embodiment of the invention, the diluent is selected from water for injection, 0.9% sodium chloride solution (NaCl), 5% dextrose solution.

Preferably in a method according to an embodiment of the invention, 40-80 mg pantoprazole sodium sesquihydrate, expressed as pantoprazole, in a volume of 1 mL or less polyethylene glycol is diluted with 10 mL of water for injection thereby obtaining a 4-8 mg/mL aqueous pantoprazole sodium sesquihydrate solution, having an osmolality of 200-300 mOsmol/kg and a pH of 9.5-10.2.

Preferably in a method according to an embodiment of the invention, 40-80 mg pantoprazole sodium sesquihydrate, expressed as pantoprazole, in polyethylene glycol is first diluted with 10 mL of water for injection and is then further diluted to a total volume of 100 mL of 0.9 sodium chloride, 5% dextrose solution thereby obtaining a 0.4-0.8 mg/mL aqueous pantoprazole sodium sesquihydrate solution, having an osmolality of 200-600 mOsmol/kg and a pH of 8.5-10.0.

In another aspect, the invention provides a packaging container, comprising one or more unit doses of the concentrated storage stable, non-aqueous composition of a pharmaceutically acceptable salt of pantoprazole according to an embodiment of the invention.

Preferably the packaging container according to an embodiment of the invention is covered with a head-space having an oxygen content below 10% oxygen, preferably below 5% oxygen, even more preferably below 2% oxygen. Headspace Oxygen Content was measured using a Fiber Optic Oxygen Transmitter (PreSens, Microx 4). The measurement was as follows: pierced the vial with the optic fiber syringe needle and measured the headspace oxygen level as a percentage (%).

Preferably, the packaging container is a glass vial or syringe or pen.

In another aspect, the invention provides a prefilled syringe comprising the concentrated, storage stable, non-aqueous composition according to an embodiment of the invention.

In a final aspect, the invention provides a method of manufacturing a concentrated, storage stable, non-aqueous pantoprazole composition according to an embodiment of the invention, comprising the step of:

- providing polyethylene glycol with an oxygen content of less than 2 ppm,
- warming the polyethylene glycol to a temperature between 45° C. and 55° C.,
- dissolving in the warmed polyethylene glycol an amount of stabilizer, preferably an alkali metal hydroxide, more preferably sodium hydroxide,
- cooling the mixture obtained in the previous step below 25° C.,
- adding to the cooled liquid mixture an amount of a pharmaceutically acceptable salt of pantoprazole to obtain a 40-80 mg/mL pantoprazole solution.

Preferably the 40-80 mg/mL pantoprazole solution is divided into portions of 1 mL or smaller and individual portions are filled into a packaging container, preferably into a dehydrogenated clear glass vial, syringe or pen.

DETAILED DESCRIPTION OF THE INVENTION

At the very outset of the detailed description, it may be understood that the ensuing description only illustrates a particular form of this invention. However, such a particular form is only exemplary embodiment, and without intending to imply any limitation on the scope of this invention. Accordingly, the description is to be understood as an exemplary embodiment and teaching of invention and not intended to be taken restrictively.

It is also to be understood that the terminology used herein is for the purpose of describing particular embodiments only and is not intended to limit the present disclosure.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number. In an embodiment, "about" can mean within one or more standard deviations, or within ±30%, 25%, 20%, 15%, 10% or 5% of the stated value.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described.

For the purposes of the present invention, the following terms are defined below: The articles "a" and "an" are used herein to refer to one or to more than one (i.e. to at least one) of the grammatical object of the article. By way of example, "an element" means one element or more than one element.

As used herein, the term "comprises" or "comprising" is generally used in the sense of include, that is to say permitting the presence of one or more features or components.

The term "excipient(s)" is used to describe an inert substance that is added to a pharmaceutical composition to make it easier to administer the active ingredient. This can include a range of substances, such as a surfactants, an tonicity agents, a pH adjusters, a buffers, a preservatives, vehicles, vegetable oils, and polyethylene glycols.

The term "formulation" or "composition" refers to a pharmaceutical formulation of pantoprazole described herein with a pharmaceutically acceptable carrier and/or excipient. The terms "formulation" or "composition" can be used interchangeably.

The term "pantoprazole" as used herein refers to "pantoprazole" or its pharmaceutically acceptable salt, or its pharmaceutically acceptable stereoisomer, or its pharmaceutically acceptable solvate, or its pharmaceutically acceptable hydrate, or its pharmaceutically acceptable anhydrate, or its pharmaceutically acceptable polymorph, or its pharmaceutically acceptable prodrug, and other similar form that is suitable for pharmaceutical use.

The term "pharmaceutically acceptable carrier" refers to a substance that is used as a carrier, vehicle, adjuvant, or solvent in the formulation of a drug, but does not cause significant irritation to the body or interfere with the biological activity of the drug. The terms "vehicle", "solvent" and "solvent system" refer to the same component(s), and the said terms can be used interchangeably.

The term "subject" includes mammals (especially humans) and other animals, such as domestic animals (e.g., household pets including cats and dogs) and non-domestic animals (such as wildlife). Each embodiment is provided by way of explanation of the invention and not by way of limitation of the invention. In fact, it will be apparent to those skilled in the art that various modifications and variations can be made to the compounds, and methods described herein without departing from the scope or spirit of the invention. For instance, features illustrated or described as part of one embodiment can be applied to another embodiment to yield a still further embodiment. Thus, it is intended that the present invention includes such modifications and variations and their equivalents.

Other objects, features, and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

The phrase "Ready-to-use" refers to any form of pantoprazole that can be directly given to a patient without the need for additional processing or dilution. The phrase "Ready-to-dilute" refers to a formulation that can be combined directly with a diluent such as a dextrose solution, a saline solution, or any other infusion medium, and then administered to a patient.

The present invention provides a composition for a stable ready-to-use and/or ready-to-dilute formulation, the composition comprising a proton pump inhibitor (PPI), a solvent system, pH adjusting agent as stabilizer. In certain embodiments, the formulation shows stability when stored under controlled room temperature conditions. In an embodiment, the formulation is a liquid injectable formulation. Further, the controlled room temperature refers to a condition when the temperature ranges between 20° C. to 25° C.

In an embodiment, any PPI may be used in the compositions. Formulations and/or the methods described herein. Examples of PPIs include, but are not limited to, Pantoprazole, Omeprazole, Lansoprazole, Rabeprazole and Esomeprazole. In some embodiments, the PPI is Pantoprazole.

In another embodiment, the present invention provides a composition comprising Pantoprazole or its pharmaceutically acceptable salt or stereoisomer thereof. In another embodiment, the composition further comprises a solvent system and an excipient. In yet another embodiment, the composition comprises a non-aqueous solvent system and pH adjusting agent as stabilizer.

In a further embodiment, the composition comprises pantoprazole or its pharmaceutically acceptable salt or stereoisomer thereof, a solvent system comprising one or more organic solvents, pH adjusting agent as stabilizer and a pharmaceutically acceptable carrier or excipient. Examples of excipient include, but are not limited to, a surfactant, an isotonicity agent, a pH adjuster, a buffer, a preservative, vegetable oil, and any combination thereof.

In certain embodiments, the composition comprises pantoprazole sodium ranging from about 4% (w/v) to about 8% (w/v).

In another embodiment, pantoprazole is dissolved in a solvent system to a concentration of more than about 40 mg/mL and up to about 80 mg/mL that provides less than one mL injection volumes. In another embodiment, the concentration of pantoprazole is about 80 mg/mL delivering 40 mg in 0.5 mL of injection volume. Lower solvent injection volume minimizes the risks associated with hypertonicity of organic solvent-based injections permitting the possibility of ready-to-use (direct intravenous injection).

In an embodiment, the solvent system comprises a non-aqueous solvent. The non-aqueous solvent comprises one or more organic solvents selected from the group comprising a glycol, glycerol, alcohol, and an amide. Examples of glycol include, but are not limited to, polyethylene glycol, propylene glycol, a combination thereof, and the like. In another embodiment, the concentration of the organic solvent ranges from about 20% (v/v) to about 100% (v/v). In some embodiments, the concentration of the organic solvent is from about 40% (v/v) to about 100% (v/v).

In certain embodiments, the glycol is propylene glycol. In further instances, the concentration of propylene glycol ranges from about 20% (v/v) to about 100% (v/v). In some embodiments, the concentration of propylene glycol is from about 40% (v/v) to about 100% (v/v).

In certain embodiments, the glycol is polyethylene glycol (PEG). Examples of PEG include, but are not limited to, PEG-200 (average molecular weight of 200 Da), PEG-300 (average molecular weight of 300 Da), PEG-400 (average molecular weight of 400 Da), PEG-600 (average molecular weight of 600 Da), PEG-800 (average molecular weight of 800 Da) and the like. In certain embodiments, the PEG is PEG-300 (average molecular weight of 300 Da), and/or PEG-400 (average molecular weight of 400 Da). In certain embodiments, concentration of the PEG may range from about 20% (v/v) to about 100% (v/v). In an embodiment, the composition comprises a combination of PEGs of different molecular weights. In some embodiments, the formulation of the present invention comprises a combination of PEG-300 and PEG-400. In some instances, the concentration of PEG-400 ranges from about 60% (v/v) to about 100% (v/v). In further instances, the concentration of PEG-300 ranges from about 60% (v/v) to about 100% (v/v).

Examples of alcohol include, but are not limited to ethanol, tertiary butyl alcohol and the like. In certain embodiments, the alcohol is ethanol. In further instances, the concentration of ethanol ranges from about 20% (v/v) to about 100% (v/v).

Examples of amide include, but are not limited to, dimethylformamide (DMF), dimethylacetamide (DMA), and the like. In certain embodiments, the amide is DMA. In certain embodiments, concentration of the amide solvent may range from about 10% (v/v) to about 40% (v/v). In certain embodiments, the organic solvent is selected from the group consisting of an ethanol, propylene glycol, polyethylene glycol-400, polyethylene glycol-300, N,N-Dimethylacetamide, and a combination thereof.

In an embodiment, the stabilizer is a pH adjusting agent selected from the group consisting of, but not limited to, sodium hydroxide, potassium hydroxide, arginine, tromethamine, meglumine, sodium citrate, sodium carbonate, sodium acetate, sodium bicarbonate, potassium bicarbonate and any combination thereof. In a further embodiment, the stabilizer is present in an amount ranging from 0.01% w/v to 5% w/v, and preferably in an amount ranging from 0.01% w/v to 2% w/v.

In an embodiment, the pH adjusting agent is soluble in polyethylene glycol (PEG), and preferably the pH adjusting agent is soluble in in polyethylene glycol 300 (PEG 300).

In an embodiment, the solvent is PEG, and the stabilizer is sodium hydroxide. Preferably, the solvent is PEG 300.

In an embodiment, the formulation is a ready-to-use and/or ready-to-dilute formulation, comprising polyethylene glycol and sodium hydroxide as stabilizer. More preferably, the formulation is a ready-to-use and/or ready-to-dilute formulation, comprising polyethylene glycol 300 and sodium hydroxide.

In some embodiments, the formulation is a ready-to-use and/or ready-to-dilute formulation, comprising PPI, PEG 300 and sodium hydroxide; wherein PPI is dissolved in a solvent system to a concentration of more than about 40 mg/mL and up to about 80 mg/mL that provides less than one mL injection volumes. In another embodiment, the concentration of PPI is about 80 mg/mL delivering 40 mg in 0.5 mL of injection volume.

In further embodiments, the formulation is a ready-to-use and/or ready-to-dilute formulation, comprising pantoprazole, PEG 300 and sodium hydroxide; wherein pantoprazole is dissolved in a solvent system to a concentration of more than about 40 mg/mL and up to about 80 mg/mL that provides less than one mL injection volumes. In another embodiment, the concentration of PPI is about 80 mg/mL delivering 40 mg in 0.5 mL of injection volume.

In an embodiment, the concentration of sodium hydroxide ranges from about 0.01 mg/mL to about 40 mg/mL, about 0.0.02 mg/mL to about 10 mg/mL or about 0.1 mg/mL to about 6 mg/mL; most preferably around 0.2 mg/mL.

In another embodiment, the composition is a stable injectable formulation comprising pantoprazole or its pharmaceutically acceptable salt or stereoisomer thereof ready for dilution with infusion solution, without any need for preparation of premix solutions.

Further, the present invention provides a process for preparing a composition comprising a PPI or its pharmaceutically acceptable salt thereof for a ready-to-use and/or ready-to-dilute formulation. In an embodiment, the process comprises mixing a PPI or its pharmaceutically acceptable salt or stereoisomer thereof with a solvent system, a stabilizer, and a pharmaceutically acceptable carrier or excipient to obtain a clear solution. The process further comprises filtering the solution, filling the filtered solution into a container. In certain embodiments, PPI or its pharmaceutically acceptable salt or stereoisomer, solvent system, stabilizer, and a pharmaceutically acceptable carrier or excipient are same as defined in any of the preceding embodiments. In an embodiment, the container refers to a closure system such as ampoules, vials, pre-filled syringes, and other suitable containers.

In certain embodiments of the process, the PPI is pantoprazole, the solvent is PEG 300, and the stabilizer is sodium hydroxide.

In yet another embodiment, the present invention provides a method for the treatment or prophylaxis of a condition or disorder in a subject in need thereof by administering an effective amount of a ready-to-use and/or ready-to-dilute formulation of the present invention. In certain embodiments, the condition or disorder refers to a disease condition that is benefited by using proton pumps. Examples of such a disorder include, but is not limited to, the condition or disorder is selected from a group comprising gastric ulcer, gastroesophageal reflux disease (GERD), and a history of erosive esophagitis (EE), Zollinger-Ellison (ZE) Syndrome in adults.

In a further aspect, the invention provides a concentrated, storage stable, non-aqueous composition of pantoprazole comprising:

- 20-80 mg of a pharmaceutically acceptable salt of pantoprazole (API), expressed in amount of pantoprazole,
- polyethylene glycol in a quantity for the dissolution of the API,
- optionally a stabilizer, preferably an alkali metal hydroxide, more preferably sodium hydroxide,
- wherein the composition is comprised in a volume equal to or smaller than 1.0 mL.

Preferably the amount of API comprised in the volume of 1 mL or less, is 25, 30, 35, 40, 45, 50, 55, 60, 65, 70, 75 mg pantoprazole; in the form of a pharmaceutically acceptable salt of pantoprazole (API).

In a preferred embodiment, the volume of the composition according to an embodiment of the invention is equal to or smaller than 0.5 mL. This is a volume suitable for injection. Preferably the composition is comprised in 0.5 mL. Preferably the volume for injection is 0.5 mL. In an alternative embodiment, the volume of the composition according to an embodiment of the invention is 0.25 mL.

In another preferred embodiment, the concentrated, storage stable, non-aqueous composition according to an embodiment of the invention has a storage stability of at least 6 months, more preferably at least 12 months, even more preferably at least 18 months, most preferably at least 24 months, measured at 25° C. and 60% relative humidity, wherein the composition contains equal to or less than 4.0% w/w of total impurities, as determined by HPLC. More preferably the level of total impurities is less than 3.5% w/w, even more preferably less than 3.0% w/w. most preferably less than 2.5% w/w.

In a preferred embodiment, the concentrated, storage stable, non-aqueous composition according to the invention contains equal or less than 2.5% w/w of impurity C, as determined by HPLC. More preferably the level of impurity C is less than 2.2% w/w; even more preferably less than 2.0% w/w; most preferably less than 1.5% w/w.

Pantoprazole and related substances are discussed in Ph. Eur. and USP Monograph for Pantoprazole Sodium Sesquihydrate Organic Impurities Test 2).

In a preferred embodiment, the pharmaceutically acceptable pantoprazole salt is the sodium salt. More preferably the pharmaceutically acceptable pantoprazole salt is pantoprazole sodium sesquihydrate.

In a preferred embodiment, the concentrated, storage stable, non-aqueous pantoprazole composition according to an embodiment of the invention comprises 40 mg of said pharmaceutically acceptable pantoprazole salt, expressed in amount of pantoprazole, in a volume of 0.5 mL.

In an embodiment, the stabilizer is a pH adjusting agent selected from the group of strong alkalis, such as alkali metal compounds, for example an alkali metal hydroxide such as sodium hydroxide, potassium hydroxide, lithium hydroxide, rubidium hydroxide and cesium hydroxide or an alkaline earth metal carbonate such as sodium carbonate, potassium carbonate, calcium hydroxide, magnesium hydroxide, or a strong basic substance such as arginine. Preferably the stabilizer is an alkali metal hydroxide, more preferably the stabilizer is sodium hydroxide.

In another embodiment, the amount of stabilizer is 0.01 to 1.50 mg/mL, preferably 0.03 to 1.20 mg/mL, more preferably is 0.05 to 0.50 mg/mL, most preferably is 0.1 to 0.3 mg/mL.

In a preferred embodiment, the amount of sodium hydroxide is 0.05 to 0.50 mg/mL, preferably 0.1 to 0.3 mg/mL. Typically, around 0.2 mg/mL.

Most preferably the composition according to an embodiment of the invention comprises 0.1 to 1.50 mg/mL sodium hydroxide, even more preferably 0.2 to 1.40 mg/mL sodium hydroxide, even more preferably 0.3 to 1.30 mg/mL, also more preferably 0.4 to 1.2 mg/mL; most preferably 0.2 mg/mL.

In a preferred embodiment, the concentrated, storage stable, non-aqueous composition of pantoprazole comprises:

- 40 mg pantoprazole, in the form of pantoprazole sodium sesquihydrate salt (API),
- polyethylene glycol in a quantity for the dissolution of the API,
- sodium hydroxide as stabilizer, preferably in an amount of 0.01 to 1.5 mg/mL, more preferably 0.03 to 1.0 mg/mL, even more preferably 0.05 to 0.50 mg/mL, most preferably 0.1 to 0.3 mg/mL,
- wherein the composition is comprised in a 0.5 mL volume.

In a preferred embodiment, the concentrated, storage stable, non-aqueous composition of pantoprazole comprises:

- 40 mg pantoprazole, in the form of pantoprazole sodium sesquihydrate salt (API),
- polyethylene glycol in a quantity for the dissolution of the API,
- sodium hydroxide as stabilizer, in an amount of 0.1 to 0.3 mg/mL,
- wherein the composition is comprised in a 0.5 mL volume.

Most preferably polyethylene glycol is the only solvent present.

In a preferred embodiment, the concentrated, storage stable, non-aqueous composition of pantoprazole comprises:

- 40 mg pantoprazole, in the form of pantoprazole sodium sesquihydrate salt (API),
- polyethylene glycol in a quantity for the dissolution of the API,
- sodium hydroxide as stabilizer, in an amount of 0.1 to 0.3 mg/mL, wherein the composition is comprised in a volume equal to 0.5 mL, and the composition has a storage stability of at least 1 year measured at 25° C. and 60% relative humidity, wherein the composition contains equal to or less than 4.0% w/w of total impurities and/or less than 2.5% w/w of impurity C, as determined by HPLC.

In a preferred embodiment, the PolyEthylene Glycol comprised in the composition according to an embodiment of the invention has an average molecular weight below 500 more preferably below 300, alternatively below 200 or 100. Most preferably the non-aqueous solvent is PEG 300 (avg Mw 300).

Preferably the Polyethylene Glycol excipient used in the present invention for the preparation of the formulation is protected from oxidation by blanketing with an inert gas, such as nitrogen or argon.

In a preferred embodiment the Polyethylene Glycol excipient used in the present invention has an ethylene glycol (EG) and diethylene glycol (DEG) content below or equal to 0.1 w/v. More preferably the liquid composition according to an embodiment of the invention has an EG and DEG content below or equal to 0.1 w/v. See FDA Guidance (May 2023), Testing of Glycerin, Propylene Glycol, Maltitol Solution, Hydrogenated Starch Hydrolysate, Sorbitol solution, and other High-Risk Drug Components for Diethylene Glycol and Ethylene Glycol. USP General Chapter 469 Ethylene Glycol, Diethylene Glycol, and Triethylene Glycol in Ethoxylated Substances provides a gas chromatography testing procedure of impurity analysis of EG/DEG.

In a preferred embodiment, the concentrated, storage stable, liquid composition of pantoprazole according to an embodiment of the invention, has a dissolved oxygen content below 10 ppm. More preferably the dissolved oxygen content is below 5 ppm, even more preferably below 2 ppm. Dissolved Oxygen content may be reduced with the use of nitrogen bubbling of the composition. Dissolved Oxygen content was measured using a Fiber Optic Oxygen Transmitter (PreSens, Microx 4). An optic fiber syringe needle was inserted into a solution for measurement and initiated the measurement of Dissolved Oxygen levels. The readings were recorded in ppm.

In a preferred embodiment, the concentrated, storage stable, liquid composition of pantoprazole according to an embodiment of the invention preferably has a water content below 4.0% w/v. More preferably the water content is below 3.0% w/v; even more preferably below 2.0% w/v; most preferably below 1.8% w/v. Water content is kept low by the selection of raw materials with low water content, especially polyethylene glycol. During the preparation and filling procedures, moisture is kept low. Advantageously storage containers are pre-rinsed and dried. Water content may be determined using a Karl Fisher water determination, known to the person skilled in the art.

In a preferred embodiment, the concentrated, storage stable, liquid composition of pantoprazole according to an embodiment of the invention, is provided for intravenous administration. This particularly refers to a composition that is physiologically acceptable, for instance with regards to osmolality and pH. The pH measurement is carried out between 23° C. and 25° C. Being an essentially non-aqueous product, pH is measured either by mixing 0.5 mL of a sample with 10 mL of carbon dioxide free water and 30 μl of saturated potassium chloride (KCl) solution (PEG USP monograph).

Preferably the pH of the composition is between 9.0 and 11.5, endpoints included; more preferably between 9.2 and 10.5; even more preferably between 9.6 and 10.2; most preferably between 9.7 and 9.9.

In a preferred embodiment the composition is free of metal scavenger. Preferably the composition is free of Na-EDTA.

In a further aspect, the invention provides uses for a composition according to an embodiment of the invention. The invention also provides methods of treatment of a composition according to an embodiment of the invention.

In an embodiment, the invention provides a concentrated, storage stable, non-aqueous composition of a pharmaceutically acceptable salt of pantoprazole according to an embodiment of the invention, for use in the treatment of a patient suffering from a gastrointestinal disease, wherein the patient is administered the 1 mL or lower of the composition intravenously without prior dilution.

In a further aspect, the invention provides a method of treatment of a patient suffering from a gastrointestinal disease comprising the step of administering a concentrated, storage stable, non-aqueous composition of pharmaceutically acceptable salt of pantoprazole according to an embodiment of the invention as a bolus injection. This is advantageous as a ready-to-use medicament is provided. It provides time saving for the hospital staff as no preparation steps are required. Dilution errors cannot be made.

In another aspect, the invention relates to a method of treatment of a patient suffering from a gastrointestinal disease comprising the step of diluting a concentrated, storage stable, non-aqueous composition of a pharmaceutically acceptable salt of pantoprazole according to an embodiment of the invention with a suitable aqueous diluent to 0.4-4.0 mg/mL pharmaceutically acceptable salt of pantoprazole, expressed as pantoprazole; thereafter administering to the patient the diluted composition obtained, as an infusion (ready-to-dilute).

In a preferred embodiment the final product has a concentration of 0.4 or 0.8 or 1.3 mg or 4 mg pantoprazole equivalents per mL final product, after dilution. Dilution can be obtained using suitable diluents.

A suitable diluent for use in this method is selected from Water for Injection (WFI; 0.9% NaCl aqueous solution, 5% dextrose solution.

In a preferred embodiment the final product has an osmolality of 250-1000 mOsmol/kg.

In a preferred embodiment the final product has a pH of 9.0 to 10.5, preferably 9.6 to 10.2, even more preferably 9.7 to 9.9.

More preferably a diluted composition, obtained by diluting a concentrated, storage stable, non-aqueous pantoprazole composition according to an embodiment of the invention, has an osmolality of 200-1000 mOsmol/kg and a pH 8.2-10.5.

Most preferably a diluted composition, obtained by diluting a concentrated, storage stable, non-aqueous pantoprazole composition according to an embodiment of the invention, has an osmolality of 220-600 mOsmol/kg and a pH 8.5-10.0.

Specifically, the invention provides a method of treatment of a patient suffering from a gastrointestinal disease comprising the step of diluting a concentrated, storage stable, non-aqueous composition of a pharmaceutically acceptable salt of pantoprazole according to an embodiment of the invention with a suitable aqueous diluent to 0.4-4.0 mg/mL pharmaceutically acceptable salt of pantoprazole, expressed as pantoprazole; thereafter administering to the patient the diluted composition obtained, as an infusion (ready-to-dilute).

In this procedure a ready-to-dilute composition is diluted to a preferred strength. There is no reconstitution time to get a solid composition, such as a lyophilized powder or a frozen infusion bag, in a condition that it can be administered as a liquid. In contradistinction, the ready-to-dilute product according to an embodiment of the invention, provides increased comfort for the hospital staff.

In a preferred embodiment the patient is administered a final product, derived from a composition according to an embodiment of the invention by dilution, that has an osmolality of 200-1000 mOsmol/kg.

In a preferred embodiment the patient is administered a final product that has a pH of 8.2 to 10.5, even more preferably 8.5-10.0.

A suitable diluent for use in this method is selected from Water for Injection (WFI; 0.9% NaCl aqueous solution, 5% dextrose solution.

Preferably the osmolality of the diluted formulation obtained, when diluted in water for injection, thereby obtaining a 4 mg/mL pantoprazole concentration, is situated between 150-600 mOsmol/kg, endpoints included. More preferably the osmolality of the diluted product obtained is 200-260 mOsmol/kg, most preferably 220-250 mOsmol/kg.

Preferably the osmolality of the diluted formulation obtained, when diluted in 0.9% sodium chloride thereby obtaining a 4 mg/mL pantoprazole concentration, is situated between 200-1000 mOsmol/kg, endpoints included. More preferably the osmolality of the diluted product obtained is-200-80 0 mOsmol/kg. even more preferably-220-750 mOsmol/kg, most preferred 220 to 650 mOsmol/kg.

Preferably in a method according to an embodiment of the invention, 40-80 mg pantoprazole sodium sesquihydrate, expressed as pantoprazole, in a volume of 1 mL or less polyethylene glycol is diluted to a total volume of 100 mL of 0.9% NaCl thereby obtaining a 4-8 mg/mL aqueous pantoprazole sodium sesquihydrate solution, having an osmolality of 200-600 mOsmol/kg and a pH of 8.4-10.0; most preferably a pH of 8.9-9.5.

Preferably in a method according to an embodiment of the invention, 40-80 mg pantoprazole sodium sesquihydrate, expressed as pantoprazole, in polyethylene glycol is first diluted with 10 mL of 0.9% NaCl or Dextrose solution and is then further diluted to a total volume of 100 mL with 0.9 sodium chloride, or5% dextrose solution thereby obtaining a 0.4-0.8 mg/mL aqueous pantoprazole sodium sesquihydrate solution, having an osmolality of 200-400 mOsmol/kg and a pH of 8.4-10.5.

Preferably in a method according to an embodiment of the invention, 40-80 mg pantoprazole sodium sesquihydrate, expressed as pantoprazole, in polyethylene glycol is first diluted with 10 mL of 0.9% sodium chloride solution and is then further diluted to a total volume of 100 mL with 0.9% sodium chloride solution thereby obtaining a 0.4-0.8 mg/mL aqueous pantoprazole sodium sesquihydrate solution, having an osmolality of 200-400 mOsmol/kg and a pH of 8.4-10.5.

Preferably in a method according to an embodiment of the invention, 40-80 mg pantoprazole sodium sesquihydrate, expressed as pantoprazole, in a polyethylene glycol solution volume of 1.0 mL, is diluted in 100 mL of an infusion bag of 0.9 sodium chloride or 5% dextrose thereby obtaining a 0.4-0.8 mg/mL aqueous pantoprazole sodium sesquihydrate solution, having an osmolality of 200-650 mOsmol/kg and a pH of 8.4-10.5.

In a further aspect, the invention provides a method of manufacturing a concentrated, storage stable, liquid composition of pantoprazole according to an embodiment of the invention, comprising the steps of:

i) optionally purging with nitrogen a polyethylene glycol solution to a dissolved oxygen content of less than 2 ppm,
ii) optionally heating the polyethylene glycol solution of step i) to 45° C.-55° C.,
iii) dissolving in polyethylene glycol a stabilizer, preferably an alkali metal hydroxide, more preferably sodium hydroxide, even more preferably sodium hydroxide sesquihydrate,
iv) optionally cooling the solution of step iii) to not more than 25° C.,
v) adding 20-80 mg of a pharmaceutically acceptable salt of pantoprazole (API), expressed in amount of pantoprazole to the cooled solution,
vi) optionally making up the volume of the solution of step v with polyethylene glycol to a desired final volume,
vii) optionally aseptically filtering the solution of step vi.

Alternatively, the invention provides a method of manufacturing a concentrated, storage stable, non-aqueous pantoprazole composition according to an embodiment of the invention, comprising the step of:

providing polyethylene glycol with an oxygen content of less than 2 ppm,
warming the polyethylene glycol to a temperature between 45° C. and 55° C.,
dissolving in the warmed polyethylene glycol an amount of stabilizer, preferably an alkali metal hydroxide, more preferably sodium hydroxide,
cooling the mixture obtained in the previous step below 25° C.,
adding to the cooled liquid mixture an amount of a pharmaceutically acceptable salt of pantoprazole to obtain a 40-80 mg/mL pantoprazole solution.

Preferably the 40-80 mg/mL pantoprazole solution is divided into portions of 1 mL or smaller and individual portions are filled into a packaging container, preferably into a dehydrogenated clear glass vial, syringe or pen.

In a further aspect, the invention provides a packaging container, comprising one or more unit doses of the concentrated storage stable, non-aqueous composition of a pharmaceutically acceptable salt of pantoprazole according to an embodiment of the invention.

Preferably the packaging container's head-space covering the concentrated storage stable, liquid pantoprazole composition, has an oxygen content below 10%; more preferably below 7%, even more preferably below 5%, most preferably below 2%. The head-space oxygen content can be obtained with the use of nitrogen purging in to the packaging container during the filling operation. Headspace Oxygen Content was measured using a Fiber Optic Oxygen Transmitter (PreSens, Microx 4). The measurement was as follows: pierced the vial with the optic fiber syringe needle and measured the headspace oxygen level as a percentage (%).

In a preferred embodiment the packaging container is a multi-dose packaging container.

Preferably the multi-dose packaging container is a glass vial, syringe, or pen. More preferably the (multi-dose) packaging container used for holding a composition according to an embodiment of the invention is provided with an inert atmosphere, e.g. nitrogen or argon.

In a final aspect, the invention provides a prefilled syringe comprising a concentrated, storage stable, liquid composition of pantoprazole according to an embodiment of the invention.

The present disclosure now being generally described, it will be more readily understood by reference to the following examples, which are included merely for purposes of illustration of certain aspects and embodiments of the present disclosure and are not intended to limit the present disclosure in any way.

EXAMPLES

Although the content of the present invention is further specifically explained using Examples, the present invention is not limited to the following Examples as long as the gist of the present invention is not exceeded. Values of various manufacturing conditions and evaluation results in the following Examples mean preferable values of an upper limit or a lower limit in the embodiments of the present invention, and a preferable range may be a range defined by a combination of the above-described upper limit or the above-described lower limit and the values of the following Examples or a combination of the values of Examples.

Examples 1 to 4

Table 1 shows a comparative illustration for different formulations of the compositions, Examples 1-4. All the examples comprise Pantoprazole dissolved in a non-aqueous solvent system. Examples 3 and 4 further comprise pH adjusting agent as stabilizer. The stability of the said formulations was assessed based on stability data obtained under accelerated, intermediate and long-term stability conditions as shown in Tables 2, 3, and 4, respectively. Thus, the stability of the said composition was assessed based on the percentage amounts (% w/w) of the related substances. Among the different types of impurities that were analysed for stability testing, the most significant impurity was Impurity C and the data for the same was analysed in addition to the total impurity content under different conditions.

Example 3 which contains sodium hydroxide shows better stability profile especially with respect to Impurity-C levels than other formulations of Examples 1 and 2, which are without sodium hydroxide. Example 3, which contains sodium hydroxide and organic solvent PEG 300, shows better stability profile especially for Impurity-C levels than Example 1 without sodium hydroxide. Example 3, which contains sodium hydroxide as the stabilizer and PEG 300 as solvent system, shows better stability profile especially for Impurity-C levels than Example 4, which contains same sodium hydroxide as pH adjusting agent but consists of propylene glycol instead of PEG 300 as the solvent system.

Alpha tocopherol was also tested as stabilizer but upon dilution with 0.9% sodium chloride solution, precipitation was formed.

The results infer that PEG, preferably PEG 300, with sodium hydroxide provides a formulation with improved stability, which can be stored at controlled room temperature of 20°-25° C. (68°-77° F.).

TABLE 1

| Compositions | | | | |
|---|---|---|---|---|
| | Quantity per mL | | | |
| Ingredients | Example 1 | Example 2 | Example 3 | Example 4 |
| API expressed in Pantoprazole equivalents | 80 mg | 80 mg | 80 mg | 80 mg |

TABLE 1-continued

| Compositions | | | | |
|---|---|---|---|---|
| | Quantity per mL | | | |
| Ingredients | Example 1 | Example 2 | Example 3 | Example 4 |
| Sodium metabisulfite | — | 2 mg | — | — |
| Sodium hydroxide | — | — | 1.145 mg | 1.2 mg |
| Polyethylene glycol 300 | Q.S. to 1 mL | Q.S. to 1 mL | Q.S. to 1 mL | — |
| Propylene glycol | — | | | Q.S. to 1 mL |
| Nominal Volume (Volume/40 mg dose) | 0.5 mL | 0.5 mL | 0.5 mL | 0.5 mL |

Q.S.: Quantity sufficient
API: pantoprazole sodium sesquihydrate

The Related Substances (% w/w) Results for the compositions provided in Table 1, are summarized in Table 2.

TABLE 2

| Accelerated Stability (40° C./75% RH) | | | | | | | | |
|---|---|---|---|---|---|---|---|---|
| | Example 1 | | Example 2 | | Example 3 | | Example 4 | |
| Degradant | Initial | 1 M | Initial | 1 M | Initial | 1 M | Initial | 1 M |
| Impurity-A | 0.095 | 0.093 | 0.087 | 0.070 | 0.084 | 0.086 | 0.084 | 0.100 |
| Impurity-B | 0.007 | 0.126 | 0.006 | 0.357 | 0.005 | 0.133 | 0.006 | 0.128 |
| Impurity-C | 0.002 | 0.332 | 0.004 | 0.447 | ND | 0.230 | 0.006 | 2.512 |
| Impurity D & F | 0.042 | 0.039 | 0.046 | 0.080 | 0.039 | 0.031 | 0.031 | 0.035 |
| Impurity E | 0.008 | 0.008 | 0.009 | 0.012 | 0.008 | 0.013 | 0.009 | 0.074 |
| Maximum Unspecified Impurity | ND | 0.032 | ND | 0.347 | 0.009 | 0.082 | ND | 0.421 |
| Total Impurities | 0.15 | 0.63 | 0.15 | 1.57 | 0.15 | 1.01 | 0.13 | 4.31 |

M: Month
ND: Not detected

TABLE 3

| Intermediate Stability (30° C./65% RH) | | | | | | |
|---|---|---|---|---|---|---|
| Related substances | Example 1 | | | Example 2 | | |
| Degradant | Initial | 1 M | 2 M | Initial | 1 M | 2 M |
| Impurity-A | 0.095 | 0.097 | 0.087 | 0.087 | 0.074 | 0.068 |
| Impurity-B | 0.007 | 0.032 | 0.059 | 0.006 | 0.060 | 0.144 |
| Impurity-C | 0.002 | 0.051 | 0.14 | 0.004 | 0.098 | 0.215 |
| Impurity D & F | 0.042 | 0.043 | 0.037 | 0.046 | 0.066 | 0.075 |
| Impurity E | 0.008 | 0.009 | 0.011 | 0.009 | 0.010 | 0.020 |
| Maximum Unspecified Impurity | ND | ND | ND | ND | 0.12 | 0.258 |
| Total Impurities | 0.15 | 0.23 | 0.33 | 0.15 | 0.54 | 0.99 |

| Related substances | Example 3 | | | Example 4 | |
|---|---|---|---|---|---|
| Degradant | Initial | 1 M | 2 M | Initial | 1 M |
| Impurity-A | 0.084 | 0.092 | 0.096 | 0.084 | 0.085 |
| Impurity-B | 0.005 | 0.028 | 0.059 | 0.006 | 0.028 |
| Impurity-C | ND | 0.011 | 0.037 | 0.006 | 0.448 |
| Impurity D & F | 0.039 | 0.029 | 0.025 | 0.031 | 0.029 |

TABLE 3-continued

| Intermediate Stability (30° C./65% RH) | | | | | |
|---|---|---|---|---|---|
| Impurity E | 0.008 | 0.011 | 0.012 | 0.009 | 0.010 |
| Maximum Unspecified Impurity | 0.009 | 0.025 | 0.040 | ND | 0.313 |
| Total Impurities | 0.15 | 0.33 | 0.43 | 0.13 | 1.16 |

ND: Not detected
M: Month(s)

TABLE 4

Long-term Stability (25° C./60% RH)

| Related substances | Example 1 | | | | Example 2 | | |
|---|---|---|---|---|---|---|---|
| Degradant | Initial | 1 M | 2 M | 3 M | Initial | 1 M | 2 M |
| Impurity-A | 0.095 | 0.095 | 0.082 | 0.088 | 0.087 | 0.077 | 0.075 |
| Impurity-B | 0.007 | 0.015 | 0.025 | 0.040 | 0.006 | 0.006 | 0.037 |
| Impurity-C | 0.002 | 0.017 | 0.053 | 0.080 | 0.004 | 0.035 | 0.068 |
| Impurity D & F | 0.042 | 0.042 | 0.037 | 0.040 | 0.046 | 0.066 | 0.064 |
| Impurity E | 0.008 | 0.009 | 0.01 | 0.011 | 0.009 | 0.010 | 0.017 |
| Maximum Unspecified Impurity | ND | ND | ND | ND | ND | 0.061 | 0.059 |
| Total Impurities | 0.15 | 0.18 | 0.21 | 0.26 | 0.15 | 0.29 | 0.32 |

| Related substances | Example 3 | | | | Example 4 | |
|---|---|---|---|---|---|---|
| Degradant | Initial | 1 M | 2 M | 3 M | Initial | 1 M |
| Impurity-A | 0.084 | 0.091 | 0.093 | 0.103 | 0.084 | 0.086 |
| Impurity-B | 0.005 | 0.011 | 0.027 | 0.045 | 0.006 | 0.021 |
| Impurity-C | ND | 0.002 | 0.001 | 0.004 | 0.006 | 0.156 |
| Impurity D & F | 0.039 | 0.027 | 0.025 | 0.028 | 0.031 | 0.028 |
| Impurity E | 0.008 | 0.011 | 0.012 | 0.010 | 0.009 | 0.012 |
| Maximum Unspecified Impurity | 0.009 | 0.016 | 0.022 | 0.025 | ND | 0.171 |
| Total Impurities | 0.15 | 0.22 | 0.26 | 0.35 | 0.13 | 0.61 |

ND: Not detected
M: Month(s)

Examples 5 to 8: NaOH Amount

Additional compositions were made, as summarized in Table 5.

Example 8 was prepared with the use of heating in view of a higher amount of sodium hydroxide used. The inventors found this has a positive impact on water content.

Based on the development work performed, the following optimized manufacturing procedure was obtained.

Manufacturing Procedure:

Step 1: The active and inactive ingredients were dispensed

Step 2: The required amount of polyethylene glycol (PEG) was collected in compounding vessel.

Step 3: PEG was purged with nitrogen to get the required dissolved Oxygen (DO) level, less than 2 ppm of oxygen content.

Step 4: When sodium hydroxide is used, PEG is heated to 45° C.-55° C. and the weighed quantity of sodium hydroxide is added to the compounding vessel, which is stirred until a clear solution is formed Step 5: PEG solution is then cooled to not more than 25° C. and the weighed amount of pantoprazole, preferably pantoprazole sodium sesquihydrate is added which is stirred until a clear solution is obtained Step 6. The volume is made up to 100% with polyethylene glycol and stirred to get uniform solution.

Step 7: The solution is aseptically filtered through 0.22 micron PVDF filter to obtain a sterile filtrate.

Step 8: The filtered bulk solution is aseptically filled into dehydrogenated clear glass vials followed by stoppering and sealing.

For the compositions summarized in Table 5, the PEG used was PEG300.

All examples comprise less than 2 ppm of oxygen content and less than 3% of oxygen in the headspace.

TABLE 5

Pantoprazole compositions with and without stabilizer

| Ingredients | Quantity per mL | | | |
|---|---|---|---|---|
| | Example 5 | Example 6** | Example 7** | Example 8** |
| API expressed in Pantoprazole equivalents | 80 mg | 80 mg | 80 mg | 80 mg |
| Sodium hydroxide | 0 mg | 0.3 mg | 1.0 mg | 1.2 mg |
| Polyethylene glycol 300 | Q.S. to 1 mL | Q.S. to 1 mL | Q.S. to 1 mL | Q.S. to 1 mL |
| Nominal Volume (Volume/40 mg dose) | 0.5 mL | 0.5 mL | 0.5 mL | 0.5 mL |

Q.S.: Quantity sufficient
API: pantoprazole sodium sesquihydrate
**heating was used during the manufacturing Samples were stored under different conditions and the assay content, sample characteristics (pH, osmolality, water content) and impurity levels were determined at regular time intervals. The results obtained under storage conditions of 25° C. and 60% Relative Humidity are provided in Table 6. With respect to impurities, the most important impurity C is reported together with the total impurities.

CONCLUSIONS

The results show that pantoprazole in PEG with sodium hydroxide provide formulations with improved stability, especially for Impurity C levels. These solutions can be stored at controlled room temperature of 20°-25° C. (68°-77° F.) for an extended period of time.

Actual results show a shelf-life of at least 6 months, under room temperature conditions. Based on extrapolation, a shelf-life of at least 2 years is expected under these storage conditions. This is commercially relevant and makes use of the product possible in a supply chain from large scale manufacturer to patient, including storage and distribution.

Based on the storage conditions at 40° C., example 8, it shows that prolonged exposure of the finished product to increased temperatures should be avoided to ensure prolonged shelf-life.

TABLE 6

Long-term Stability testing (25° C./60% RH)

| Product characteristic | Example 5 | | | | | | Example 6 | | | | | |
|---|---|---|---|---|---|---|---|---|---|---|---|---|
| over time (Months) | 0 M | 3 M | 6 M | 12 M* | 18 M* | 24 M* | 0 M | 3 M | 6 M | 12 M* | 18 M* | 24 M* |
| pH at 23-25° C. (Dilution to 4 mg/mL with 0.9% Sodium chloride Solution) | 9.44 | 9.60 | 9.48 | — | — | — | 9.57 | 9.73 | — | — | — | — |
| Osmolality (mOsmol/kg) (Dilution to 4 mg/mL with 0.9% Sodium chloride Solution) | 518 | 442 | 423 | — | — | — | 528 | 531 | 545 | — | — | — |
| Water content (% w/w) | — | — | — | — | — | — | 1.72 | 1.59 | 1.63 | — | — | — |
| Impurity C (%) | ND | 0.063 | 0.186 | 1.013* | 1.571* | 2.129* | 0.001 | 0.024 | 0.083 | 0.446* | 0.692* | 0.938* |
| Total impurities (%) | 0.13 | 0.24 | 0.35 | — | — | — | 0.07 | 0.06 | 0.08 | — | — | — |

| Product characteristic | Example 7 | | | | | | Example 8** | | | | | |
|---|---|---|---|---|---|---|---|---|---|---|---|---|
| over time (Months) | 0 M | 3 M | 6 M | 12 M* | 18 M* | 24 M* | 0 M | 3 M | 6 M | 12 M* | 18 M* | 24 M* |
| pH at 23-25° C. (Dilution to 4 mg/mL with 0.9% Sodium chloride Solution) | 9.69 | — | 10.24# | — | — | — | 10.81 | 10.50 | 10.47 | — | — | — |
| Osmolality (mOsmol/kg) (Dilution to 4 mg/mL with 0.9% Sodium chloride Solution) | 524 | — | 558 | — | — | — | 543 | 545 | 552 | — | — | — |
| Water content (%, w/w) | 1.5 | — | 1.43 | — | — | — | 0.85 | 0.95 | 0.95 | — | — | — |
| Impurity C (%) | ND | 0.002 | 0.029 | 0.155* | 0.242* | 0.329* | ND | 0.002 | 0.004 | 0.022* | 0.034* | 0.046* |
| Total impurities (%) | 0.07 | 0.11 | 0.25 | — | — | — | 0.07 | 0.11 | 0.28 | | | |

*extrapolated data

**heating was used during preparation of the composition

ND: Not detected

API: pantoprazole sodium sesquihydrate

M: Month(s)

TABLE 7

Accelerated Storage Stability testing (40° C./75% RH)

| Product characteristic | Example 5 | | | | | Example 6 | | | | |
|---|---|---|---|---|---|---|---|---|---|---|
| over time (Months) | 0 M | 1 M | 2 M | 3 M | 6 M | 0 M | 1 M | 2 M | 3 M | 6 M |
| pH at 23-25° C. (Dilution to 4 mg/mL with 0.9% Sodium chloride Solution) | — | — | — | — | — | 9.57 | 9.67 | — | 9.79 | — |
| Osmolality (mOsmol/kg) (Dilution to 4 mg/mL with 0.9% Sodium chloride Solution) | 518 | — | — | — | — | 528 | 542 | — | 537 | 543 |
| Water content (% w/w) | — | — | — | — | — | 1.72 | 1.66 | — | 1.67 | 1.80 |
| Impurity C (%) | ND | 0.329 | — | — | — | 0.001 | 0.220 | — | 0.896 | 1.596 |
| Total impurities (%) | 0.13 | 0.54 | | — | — | 0.07 | 0.59 | — | 2.07- | 2.88 |

| Product characteristic | Example 7 | | | | | Example 8** | | | | |
|---|---|---|---|---|---|---|---|---|---|---|
| over time (Months) | 0 M | 1 M | 2 M | 3 M | 6 M | 0 M | 1 M | 2 M | 3 M | 6 M |
| pH at 23-25° C. (Dilution to 4 mg/mL with 0.9% Sodium chloride Solution) | 9.69 | — | — | — | — | 10.81 | 10.57 | 10.26 | 10.65 | 10.56 |

TABLE 7-continued

| Accelerated Storage Stability testing (40° C./75% RH) | | | | | | | | | | |
|---|---|---|---|---|---|---|---|---|---|---|
| Osmolality (mOsmol/kg) (Dilution to 4 mg/mL with 0.9% Sodium chloride Solution) | 524 | — | — | — | — | 543 | 541 | 527 | 551 | 519 |
| Water content (% w/w) | 1.5 | — | — | — | — | 0.85 | 0.95 | 1.01 | 1.04 | 1.14 |
| Impurity C (%) | ND | 0.092 | — | 0.776 | 1.844 | ND | 0.055 | 0.123 | 0.191 | 0.486 |
| Total impurities (%) | 0.07 | 0.63 | — | 1.59 | 3.62 | 0.07 | 0.76 | 1.78 | 2.38 | 4.31 |

API: pantoprazole sodium sesquihydrate;
ND: Not detected;
M: Month(s)|

Examples 9 to 11: Osmolality

Following formulations were prepared as mentioned in Table 8 below. Further, osmolality was measured for each formulation at four different dilution concentrations recommended, by employing freezing-point depression method. Results are shown in the following Table 9. Dilutions were carried out either by using water for injection, 0.9% sodium chloride solution (NaCl) or 5% dextrose solution.

TABLE 8

| Compositions | | | | | | | |
|---|---|---|---|---|---|---|---|
| | Quantity per mL | | | | | | |
| Ingredients | Ex 5 | Ex 6 | Ex 7 | Ex 8 | Ex 9 (not part of invention) | Ex 10 (not part of the invention) | Ex 11 |
| API, expressed in Pantoprazole equivalents | 80 mg | 80 mg | 80 mg | 80 mg | 8.0 mg | 20 mg | 40 mg |
| N,N-DMAC | — | — | — | — | 30% v/v | — | — |
| Ethanol | — | — | — | — | Q.S. to 1 mL | — | — |
| PEG 300 | Q.S. to 1 mL | Q.S. to 1 mL | Q.S. to 1 mL | Q.S. to 1 mL | — | Q.S. to 1 mL | Q.S. to 1 mL |
| NaOH | — | 0.3 mg | 1.0 mg | 1.2 mg | — | — | — |
| Nominal Volume (Volume/40 mg dose) | 0.5 mL | 0.5 mL | 0.5 mL | 0.5 mL | 5 mL | 2 mL | 1 mL |

API: pantoprazole sodium sesquihydrate
Q.S.: Quantity Sufficient

As can be seen from Table 9 below, in Example 9, the formulation did not freeze at 4 mg/mL and 0.8 mg/mL concentrations and showed very high theoretically calculated osmolality values. In Example 10, composition showed significant reduction in the Osmolality values. However, osmolality values for Example 10 were still beyond the tolerable osmolality range for 4 mg/mL in In Examples 11 and 5, compositions showed at all the dilution concentrations, the osmolality values below the recommended upper limit of 1000 mOsm/kg for small-volume injections (≤100 mL) for intravenous administration. Further, as can be seen for Example 5, 6, 7 & 8 values of Osmolality were well below the 1000 mOsm/kg and close to osmolality of reconstituted solution of Protonix iv, which is the US Reference Listed Drug (RLD).

TABLE 9

| Osmolality results of prepared formulations, expressed in mOsmol/kg, compared to the commercial product Protonix IV: | | | | | | | | |
|---|---|---|---|---|---|---|---|---|
| | Osmolality (mOsmol/kg) | | | | | | | |
| Dilution concentration + diluent used | Dilutions of Example 5 | Dilutions of Example 6 | Dilutions of Example 7 | Dilutions of Example 8 | Dilutions of Example 9 | Dilutions of Example 10 | Dilutions of Example 11 | Dilutions of Protonix IV (Reference) |
| Dilution in 10 ml 0.9% NaCl | | | 524 | 543 | | | | |

TABLE 9-continued

Osmolality results of prepared formulations, expressed in mOsmol/kg, compared to the commercial product Protonix IV:

| Dilution concentration + diluent used | Osmolality (mOsmol/kg) Dilutions of Example 5 | Dilutions of Example 6 | Dilutions of Example 7 | Dilutions of Example 8 | Dilutions of Example 9 | Dilutions of Example 10 | Dilutions of Example 11 | Dilutions of Protonix IV (Reference) |
|---|---|---|---|---|---|---|---|---|
| 4 mg/mL 0.9% NaCl | 512 | 528 | | | Approx. 7780@ | 1757 | 845 | 307 |
| 4 mg/mL water | 246 | 203 | — | — | — | 1685 | 525 | — |
| 0.4 mg/mL 0.9% NaCl | 315 | — | — | — | 2193 | 362 | 364 | 285 |
| 0.4 mg/mL 5% dextrose | 337 | — | — | — | — | 414 | 359 | 310 |
| 1.3 mg/mL 0.9% NaCl | 404 | — | — | — | — | 656 | 457 | 301 |
| 0.8 mg/mL 0.9% NaCl | 332 | — | — | — | Approx. 1800@ | 454 | 364 | 289 |
| 0.8 mg/mL 5% dextrose | 365 | — | — | — | — | 538 | 413 | 312 |

@Theoretical Osmolality value presented as the sample did not freeze

Example 12: More Preferred Compositions (Diluted, Undiluted)

TABLE 10 most preferred composition

| Ingredients | Undiluted | Diluted | Diluted |
|---|---|---|---|
| API expressed in Pantoprazole equivalents | 20-40 mg | 2-4 mg | 0.2-2.0 mg |
| Sodium hydroxide | 0.15-0.75 mg | 0.015-0.075 mg | 0.001-0.008 mg |
| Polyethylene glycol 300 | Q.S. to 0.5 mL | 50-60 mg | 5-6 mg |
| Volume | 0.5 mL | X 10 | X 100 |
| Diluent | Not applicable | WFI<br>0.9% NaCl<br>5% dextrose | WFI<br>0.9% NaCl<br>5% dextrose |
| Osmolality (mOsmol/kg) | Measurement not feasible | 200-620 | 200-400 |
| pH | 9.0-10.5* | 9.0-10.2 | 8.5-9.7 |

WFI: Water for Injection
API: pantoprazole sodium sesquihydrate
Density PEG 300: 1.127 g/mL
Q.S.: Quantity Sufficient
*pH is tested as per the method equivalent to USP recommended procedure for pH measurement of PEG (0.5 mL sample + 10 mL of water + 30 μL of saturated potassium chloride solution).

Example 13: Use of Compositions in Clinical Practice-Undiluted

The inventors have found that a composition according to the invention, wherein a highly concentrated pantoprazole composition (40-80 mg/mL) is comprised in non-aqueous polyethylene glycol solvent can be directly administered intravenously to a patient provided the volume is kept below 1 mL, preferably corresponds to 0.5 mL. This overcomes the prejudice that pantoprazole-based PEG solutions need to be diluted prior to use in a human patient.

A patient suffering from a gastrointestinal disease, in need of proton pump inhibition, is prescribed pantoprazole iv. The patient is administered a composition according to the invention intravenously by direct injection of 0.5 mL of a stabilized 40-80 mg/mL pantoprazole in PEG solution.

The product of the invention has the advantage of being directly available to the care giver and patient. No prior dilution of a lyophilized composition is required. No thawing of a frozen infusion bag is required for the treatment to become available.

Example 14: Use of Compositions in Clinical Practice-Diluted

Alternatively, the 0.5 mL volume of a stabilized 40-80 mg/mL pantoprazole in PEG solution is introduced into an infusion bag. For example a syringe filled with the 0.5 mL composition is injected into the infusion bag. The preferred dilution factor is ×10 to ×100.

As can be seen in the examples, the selection of a suitable diluent provides a physiologically acceptable formulation (osmolality, pH), without the need for separate addition of an osmolality adjuster or pH adjuster.

This method of treatment has the advantage that it is compatible with currently existing procedures of administering pantoprazole by infusion. Use of a composition according to an embodiment of the invention is advantageous as it is immediately available as liquid, so the concern with particles when diluting a lyophilized composition are avoided.

Example 15: Most Preferred Compositions (Diluted, Undiluted)

The composition details of the optimized formulation of Pantoprazole Sodium Injection, 40 mg/0.5 mL (Heating is required) are provided in Table 11.

TABLE 11 most preferred undiluted compositions

| Ingredients | Qty./mL | Qty./mL |
|---|---|---|
| Pantoprazole USP<br>(Pantoprazole Sodium Sesquihydrate) | 80.0 mg<br>(90.2 mg) | 40.0 mg<br>(45.1 mg) |
| Sodium Hydroxide | 0.2 mg | 0.1 mg |
| Polyethylene glycol 300 | q.s. to 1 mL | q.s. to 0.5 mL |

q.s.: Quantity sufficient

Example 16: Overview of pH and Osmolality for Diluted Solutions Obtained from a Concentrated Formulation of Table 11, with 0.2 mg/mL NaOH

Example 16. A Water for Injections (4 mg/mL; Only Applicable Dilution Concentration)

TABLE 12

| | pH | Osmolality |
|---|---|---|
| Preferred | 9.0-10.5 | 200-260 |
| Most preferred | 9.5-9.9 | 220-250 |

Example 16.b 0.9% NaCl (4 mg/mL)

TABLE 13

| | pH | Osmolality |
|---|---|---|
| Preferred | 9.0-10.5 | 500-600 |
| Most preferred | 9.5-10.0 | 530-570 |

Example 16.c 0.9% NaCl (0.4 mg/mL)

TABLE 14

| | pH | Osmolality |
|---|---|---|
| Preferred | 8.4-10.0 | 270-380 |
| Most preferred | 8.9-9.5 | 300-350 |

Example 16.d Dextrose (4 mg/mL)

TABLE 15

| | pH | Osmolality |
|---|---|---|
| Preferred | 9.0-10.5 | 520-620 |
| Most preferred | 9.5-10.0 | 560-600 |

Example 16.e Dextrose (0.4 mg/mL)

TABLE 16

| | pH | Osmolality |
|---|---|---|
| Preferred | 8.2-9.6 | 270-380 |
| Most preferred | 8.5-9.3 | 300-350 |

Example 17: Observed Osmolality and pH Values after Dilution of Formulation According to Table 11

TABLE 17

Osmolality and pH values for dilutions obtained

| Diluents | Concentration | pH | Osmolality (mOsmol/kg) |
|---|---|---|---|
| WFI | 4 mg/mL | 9.77 | 234 |
| 0.9% Sodium | 4 mg/mL | 9.76 | 550 |
| Chloride | 0.4 mg/mL | 9.14 | 324 |
| Injection IP | | | |
| 5% Dextrose | 4 mg/mL | 9.50 | 594 |
| Injection IP | 0.4 mg/mL | 8.82 | 336 |

The invention claimed is:

1. A concentrated, storage stable, non-aqueous, liquid composition of pantoprazole comprising:

(a) a solute, comprising: 20-80 mg of preformed pantoprazole sodium salt (API), expressed in amount of pantoprazole;

(b) a solution, comprising:

(i) polyethylene glycol in a quantity for the dissolution of the API; and, (ii) 0.03 to 1.20 mg/mL of sodium hydroxide to stabilize the API;

wherein the concentrated, storage stable, non-aqueous, liquid composition is comprised in a volume equal to or smaller than 1.0 mL;

wherein the concentrated, storage stable, non-aqueous composition is a ready-to-use or a ready-to-dilute injectable composition.

2. The composition of claim 1, wherein the volume is equal to or smaller than 0.5 mL.

3. The composition of claim 1, having a storage stability of at least 1 year measured at 25° C. and 60% relative humidity, wherein the composition contains equal to or less than 4.0% w/w of total impurities, as determined by HPLC.

4. The composition of claim 1, wherein the composition contains equal or less than 2.5% w/w of impurity C, as determined by HPLC.

5. The composition of claim 1, wherein the pharmaceutically acceptable salt of pantoprazole salt is pantoprazole sodium sesquihydrate.

6. The composition of claim 1, wherein 40 mg of said pharmaceutically acceptable salt of pantoprazole (API) expressed in amount of pantoprazole is comprised in a volume of 0.5 mL.

7. The composition of claim 1, wherein the concentration of sodium hydroxide is 0.05 to 0.50 mg/mL.

8. The composition of claim 1, wherein the concentration of sodium hydroxide is 0.1 to 0.3 mg/mL.

9. The composition of claim 1, wherein the polyethylene glycol has an average molecular weight below 500.

10. The composition of claim 1, wherein the composition, comprises less than 10 ppm dissolved oxygen.

11. The composition of claim 1, wherein the composition, comprises water equal to or below 4.0% w/v.

* * * * *